(12) United States Patent
Dyall et al.

(10) Patent No.: US 6,750,009 B2
(45) Date of Patent: Jun. 15, 2004

(54) MULTIPLE VIRAL REPLICON CULTURE SYSTEMS

(75) Inventors: Julie Dyall, Chesterfield, MO (US); Charles P. Romano, Chesterfield, MO (US); Paul D. Olivo, St. Louis, MO (US); Robert M. Roth, St. Louis, MO (US)

(73) Assignee: Apath, LLC, St. Louis, MO (US)

( * ) Notice: Subject to any disclaimer, the term of this patent is extended or adjusted under 35 U.S.C. 154(b) by 0 days.

(21) Appl. No.: 10/060,941

(22) Filed: Jan. 29, 2002

(65) Prior Publication Data

US 2003/0152912 A1 Aug. 14, 2003

(51) Int. Cl.[7] .............................. C12Q 1/70; C12N 5/06; C12N 5/10
(52) U.S. Cl. ........................... 435/5; 435/347; 435/373; 435/455
(58) Field of Search ........................... 435/5, 347, 373, 435/455

(56) References Cited

U.S. PATENT DOCUMENTS

| | | | | |
|---|---|---|---|---|
| 5,723,319 A | * | 3/1998 | King et al. .................. | 435/69.3 |
| 6,168,915 B1 | * | 1/2001 | Scholl et al. .................. | 435/5 |
| 6,270,958 B1 | * | 8/2001 | Olivo et al. .................. | 435/5 |
| 2002/0034732 A1 | * | 3/2002 | Capon et al. .................. | 435/5 |

OTHER PUBLICATIONS

Agapov, E. V. et al., Noncytopathic Sindbis virus RNA vectors for heterologous gene expression. Proc. Natl. Acad. Sci. USA. 95:12989–12994 (1998).
Blight, K. J. et al., Efficient initiation of HCV RNA replication in cell culture. Science. 290:1972–4 (2000).
Bredenbeek, P. J. et al., Sindbis virus expression vectors: packaging of RNA replicons by using defective helper RNAs. J. Virol. 67(11):6439–46 (1993).
Burgart, L. J. et al., Multiplex polymerase chain reaction. Mod. Pathol. 5(3):320–3 (1992).
Collins, P. L. et al. Transcription elongation factor of respiratory syncytial virus, a nonsegmented negative–strand RNA virus. Proc. Natl. Acad. Sci. USA. 93:81–85 (1996).
Elnifro, E. M. et al., Multiplex PCR: optimization and application in diagnostic virology. Clin. Microbiol. Rev. 13(4):559–70 (2000).
Frolov, I. et al., 1999. Selection of RNA replicons capable of persistent noncytopathic replication in mammalian cells. J. Virol. 73(5):3854–65 (1999).
Frolov, I. et al., Alphavirus–based expression vectors: strategies and applications. Proc. Natl. Acad. Sci. USA. 93:11371–7 (1996).
Grentzmann, G. et al., A dual–luciferase reporter system for studying recoding signals. RNA. 4:479–86 (1998).
Fan, J. et al., Rapid simultaneous diagnosis of infections with Respiratory Syncytial Viruses A and B, Influenza Viruses A and B, and Human Parainfluenza Virus types 1, 2, and 3 by multiplex quantitative reverse transcription– polymerase chain reaction–enzyme hybridization assay (Hexaplex). Clin. Infect. Dis.. 26:1397–402 (1998).
Grondahl, B. et al., Rapid identification of nine microorganisms causing acute respiratory tract infections by single–tube multiplex reverse transcription–PCR: feasibility study. J. Clin. Microbiol. 37(1):1–7 (1999).
Rice, C. M., et al. 1987. Production of infectious RNA transcripts from Sindbis virus cDNA clones: mapping of lethal mutations, rescue of a temperature–sensitive marker, and in vitro mutagenesis to generate defined mutants J Virol. 61:3809–19.
Rice, C. M., et al. 1989. Transcription of infectious yellow fever RNA from full–length cDNA templates produced by in vitro ligation New Biol. 1:285–96.
Jungkind, D., 1996. Evaluation of automated COBAS AMPLICOR PCR system for detection of several infectious agents and its impact on laboratory management J Clin Microbiol. 34:2778–83.
Grondahl, et al. 1999. Rapid identification of nine microorganisms causing acute respiratory tract infections by single–tube multiplex reverse transcription–PCR: feasibility study J Clin Microbiol. 37:1–7.
Parsons, S. J., 2000. Use of a dual firefly and Renilla luciferase reporter gene assay to simultaneously determine drug selectivity at human corticotrophin releasing hormone 1 and 2 receptors Anal Biochem. 281:187–92.
Plumpton M., et al. 1995 A high capacity assay for inhibitors of human papillomavirus DNA replication. Biotechnology (NY) Nov; 13(11):1210–4.

* cited by examiner

*Primary Examiner*—Donna C. Wortman
(74) *Attorney, Agent, or Firm*—Amster, Rothstein & Ebenstein LLP; Elie H. Gendloff

(57) ABSTRACT

Methods and compositions are provided for screening candidate antiviral agents using cells containing subgenomic viral replication systems such as replicons and minigenomes. The methods involve the simultaneous assay of more than one subgenomic viral replication system. Compositions useful for these methods are also provided.

23 Claims, 3 Drawing Sheets

FIG. 2

Pure YFR Culture (YFV Primers)

| IFN Conc. | % Control |
|---|---|
| Untreated | 100.00 |
| 1 IU/ml | 92.64 |
| 10 IU/ml | 58.68 |
| 100 IU/ml | 53.99 |

Mixed Culture (YFV Primers)

| IFN Conc. | % Control |
|---|---|
| Untreated | 100.00 |
| 1 IU/ml | 84.15 |
| 10 IU/ml | 60.65 |
| 100 IU/ml | 55.55 |

MULTIPLE VIRAL REPLICON CULTURE SYSTEMS

BACKGROUND

1. Field of the Invention

The present invention generally relates to methods and compositions for screening for antiviral compounds using cell cultures. More specifically, the invention relates to the use of multiple cell cultures harboring multiple subgenomic viral replication systems to evaluate compounds for antiviral activity.

2. Description of the Related Art

REFERENCES CITED

1. Agapov, E. V., I. Frolov, B. D. Lindenbach, B. M. Pragai, S. Schlesinger, and C. M. Rice 1998. Noncytopathic Sindbis virus RNA vectors for heterologous gene expression Proc Natl Acad Sci USA. 95:12989–94.
2. Arroyo, J. I., S. A. Apperson, C. B. Cropp, B. J. Marafino, Jr., T. P. Monath, R. B. Tesh, R. E. Shope, and M. A. Garcia-Blanco 1988. Effect of human gamma interferon on yellow fever virus infection Am J Trop Med Hyg. 38:647–50.
3. Ballart, I., D. Eschle, R. Cattaneo, A. Schmid, M. Metzler, J. Chan, S. Pifko-Hirst, S. A. Udem, and M. A. Billeter 1990. Infectious measles virus from cloned cDNA Embo J. 9:379–84.
4. Barclay, W., Q. Li, G. Hutchinson, D. Moon, A. Richardson, N. Percy, J. W. Almond, and D. J. Evans 1998. Encapsidation studies of poliovirus subgenomic replicons J Gen Virol. 79:1725–34.
5. Behrens, S. E., C. W. Grassmann, H. J. Thiel, G. Meyers, and N. Tautz 1998. Characterization of an autonomous subgenomic pestivirus RNA replicon J Virol. 72:2364–72.
6. Blight, K. J., A. A. Kolykhalov, and C. M. Rice 2000. Efficient initiation of HCV RNA replication in cell culture Science. 290:1972–4.
7. Bredenbeek, P. J., I. Frolov, C. M. Rice, and S. Schlesinger 1993. Sindbis virus expression vectors: packaging of RNA replicons by using defective helper RNAs J Virol. 67:6439–46.
8. Bronstein, I., C. S. Martin, J. J. Fortin, C. E. Olesen, and J. C. Voyta 1996. Chemiluminescence: sensitive detection technology for reporter gene assays Clin Chem. 42:1542–6.
9. Burgart, L. J., R. A. Robinson, M. J. Heller, W. W. Wilke, O. K. Iakoubova, and J. C. Cheville 1992. Multiplex polymerase chain reaction Mod Pathol. 5:320–3.
10. Camenisch, G., M. Gruber, G. Donoho, P. Van Sloun, R. H. Wenger, and M. Gassmann 1996. A polyoma-based episomal vector efficiently expresses exogenous genes in mouse embryonic stem cells Nucleic Acids Res. 24:3707–13.
11. Clarke, D. K., M. S. Sidhu, J. E. Johnson, and S. A. Udem 2000. Rescue of mumps virus from cDNA J Virol. 74:4831–8.
12. Collins, P. L., M. G. Hill, E. Camargo, H. Grosfeld, R. M. Chanock, and B. R. Murphy 1995. Production of infectious human respiratory syncytial virus from cloned cDNA confirms an essential role for the transcription elongation factor from the 5' proximal open reading frame of the M2 mRNA in gene expression and provides a capability for vaccine development Proc Natl Acad Sci USA. 92:11563–7.
13. Collins, P. L., M. G. Hill, J. Cristina, and H. Grosfeld 1996. Transcription elongation factor of respiratory syncytial virus, a nonsegmented negative-strand RNA virus Proc. Natl. Acad. Sci. USA. 93:81–85.
14. Constantinescu, N. 1991. [Molecular mechanisms of the antiviral effect of interferon] Rev Roum Virol. 42:191–213.
15. Conzelmann, K. K., and M. Schnell 1994. Rescue of synthetic genomic RNA analogs of rabies virus by plasmid-encoded proteins J Virol. 68:713–9.
16. Corey, D. R. 1997. Peptide nucleic acids: expanding the scope of nucleic acid recognition Trends Biotechnol. 15:224–9.
17. Davis, N. L., F. B. Grieder, J. F. Smith, G. F. Greenwald, M. L. Valenski, D. C. Sellon, P. C. Charles, and R. E. Johnston 1994. A molecular genetic approach to the study of Venezuelan equine encephalitis virus pathogenesis Arch Virol Suppl. 9:99–109.
18. Davis, N. L., L. V. Willis, J. F. Smith, and R. E. Johnston 1989. In vitro synthesis of infectious Venezuelan equine encephalitis virus RNA from a cDNA clone: analysis of a viable deletion mutant Virology. 171:189–204.
19. dos Santos, C. N., P. R. Post, R. Carvalho, Ferreira, II, C. M. Rice, and R. Galler 1995. Complete nucleotide sequence of yellow fever virus vaccine strains 17DD and 17D-213 Virus Res. 35:35–41.
20. Dryga, S. A., O. A. Dryga, and S. Schlesinger 1997. Identification of mutations in a Sindbis virus variant able to establish persistent infection in BHK cells: the importance of a mutation in the nsP2 gene Virology. 228:74–83.
21. Elnifro, E. M., A. M. Ashshi, R. J. Cooper, and P. E. Klapper 2000. Multiplex PCR: optimization and application in diagnostic virology Clin Microbiol Rev. 13:559–70.
22. Elroy-Stein, O., T. R. Fuerst, and B. Moss 1989. Cap-independent translation of mRNA conferred by encephalomyocarditis virus 5' sequence improves the performance of the vaccinia virus/bacteriophage T7 hybrid expression system Proc Natl Acad Sci USA. 86:6126–30.
23. Fan, J., K. J. Henrickson, and L. L. Savatski 1998. Rapid simultaneous diagnosis of infections with respiratory syncytial viruses A and B, influenza viruses A and B, and human parainfluenza virus types 1, 2, and 3 by multiplex quantitative reverse transcription-polymerase chain reaction-enzyme hybridization assay (Hexaplex) Clin Infect Dis. 26:1397–402.
24. Frolov, I., E. Agapov, T. A. Hoffman, Jr., B. M. Pragai, M. Lippa, S. Schlesinger, and C. M. Rice 1999. Selection of RNA replicons capable of persistent noncytopathic replication in mammalian cells J Virol. 73:3854–65.
25. Frolov, I., T. A. Hoffman, B. M. Pragai, S. A. Dryga, H. V. Huang, S. Schlesinger, and C. M. Rice 1996. Alphavirus-based expression vectors: strategies and applications Proc Natl Acad Sci USA. 93:11371–7.
26. Geierstanger, B. H., M. Mrksich, P. B. Dervan, and D. E. Wemmer 1996. Extending the recognition site of designed minor groove binding molecules Nat Struct Biol. 3:321–4.
27. Geigenmuller, U., N. H. Ginzton, and S. M. Matsui 1997. Construction of a genome-length cDNA clone for human astrovirus serotype 1 and synthesis of infectious RNA transcripts J Virol. 71:1713–7.
28. Gow, J. W., M. M. McGill, W. M. Behan, and P. O. Behan 1996. Long RT-PCR amplification of full-length enterovirus genome Biotechniques. 20:582–4.
29. Grentzmann, G., J. A. Ingram, P. J. Kelly, R. F. Gesteland, and J. F. Atkins 1998. A dual-luciferase reporter system for studying recoding signals Rna. 4:479–86.

30. Grondahl, B., W. Puppe, A. Hoppe, I. Kuhne, J. A. Weigl, and H. J. Schmitt 1999. Rapid identification of nine microorganisms causing acute respiratory tract infections by single-tube multiplex reverse transcription-PCR: feasibility study J Clin Microbiol. 37:1–7.
31. Grosfeld, H., M. G. Hill, and P. L. Collins 1995. RNA replication by respiratory syncytial virus (RSV) is directed by the N, P, and L proteins; Ttranscription also occurs under these conditions but requires RSV superinfection for efficient synthesis of full-length mRNA J. Virol. 69:5677–5686.
32. Johnson, K. L., and L. A. Ball 1997. Replication of flock house virus RNAs from primary transcripts made in cells by RNA polymerase II J Virol. 71:3323–7.
33. Jungkind, D., S. Direnzo, K. G. Beavis, and N. S. Silverman 1996. Evaluation of automated COBAS AMPLICOR PCR system for detection of several infectious agents and its impact on laboratory management J Clin Microbiol. 34:2778–83.
34. Kapoor, M., L. Zhang, P. M. Mohan, and R. Padmanabhan 1995. Synthesis and characterization of an infectious dengue virus type-2 RNA genome (New Guinea C strain) Gene. 162:175–80.
35. Khromykh, A. A., and E. G. Westaway 1997. Subgenomic replicons of the flavivirus Kunjin: construction and applications J Virol. 71:1497–505.
36. Kinney, R. M., S. Butrapet, G. J. Chang, K. R. Tsuchiya, J. T. Roehrig, N. Bhamarapravati, and D. J. Gubler 1997. Construction of infectious cDNA clones for dengue 2 virus: strain 16681 and its attenuated vaccine derivative, strain PDK-53 Virology. 230:300–8.
37. Kwong, A. D., and N. Frenkel 1984. Herpes simplex virus amplicon: effect of size on replication of constructed defective genomes containing eucaryotic DNA sequences J Virol. 51:595–603.
38. Lai, C. J., B. T. Zhao, H. Hori, and M. Bray 1991. Infectious RNA transcribed from stably cloned full-length cDNA of dengue type 4 virus Proc Natl Acad Sci USA. 88:5139–43.
39. Lee, K. J., I. S. Novella, M. N. Teng, M. B. Oldstone, and J. C. de La Torre 2000. NP and L proteins of lymphocytic choriomeningitis virus (LCMV) are sufficient for efficient transcription and replication of LCMV genomic RNA analogs J Virol. 74:3470–7.
40. Liljestrom, P., and H. Garoff 1991. A new generation of animal cell expression vectors based on the Semliki Forest virus replicon Biotechnology (NY). 9:1356–61.
41. Lindberg, A. M., C. Polacek, and S. Johansson 1997. Amplification and cloning of complete enterovirus genomes by long distance PCR J Virol Methods. 65:191–9.
42. Lindenbach, B. D., and C. M. Rice 1997. trans-Complementation of yellow fever virus NS1 reveals a role in early RNA replication J Virol. 71:9608–17.
43. Lohmann, V., F. Korner, A. Dobierzewska, and R. Bartenschlager 2001. Mutations in hepatitis C virus RNAs conferring cell culture adaptation J Virol. 75:1437–49.
44. Lohmann, V., F. Korner, J. Koch, U. Herian, L. Theilmann, and R. Bartenschlager 1999. Replication of subgenomic hepatitis C virus RNAs in a hepatoma cell line [see comments] Science. 285:110–3.
45. Lu, B., and H. J. Federoff 1995. Herpes simplex virus type 1 amplicon vectors with glucocorticoid-inducible gene expression Hum Gene Ther. 6:419–28.
46. MacDonald, G. H., and R. E. Johnston 2000. Role of dendritic cell targeting in Venezuelan equine encephalitis virus pathogenesis J Virol. 74:914–22.
47. Mackenzie, J. M., A. A. Khromykh, and E. G. Westaway 2001. Stable expression of noncytopathic Kunjin replicons simulates both ultrastructural and biochemical characteristics observed during replication of Kunjin virus Virology. 279:161–72.
48. Martino, T. A., R. Tellier, M. Petric, D. M. Irwin, A. Afshar, and P. P. Liu 1999. The complete consensus sequence of coxsackievirus B6 and generation of infectious clones by long RT-PCR Virus Res. 64:77–86.
49. Muhlberger, E., M. Weik, V. E. Volchkov, H. D. Klenk, and S. Becker 1999. Comparison of the transcription and replication strategies of marburg virus and Ebola virus by using artificial replication systems J Virol. 73:2333–42.
50. Myers, T. M., V. G. Kolupaeva, E. Mendez, S. G. Baginski, I. Frolov, C. U. Hellen, and C. M. Rice 2001. Efficient translation initiation is required for replication of bovine viral diarrhea virus subgenomic replicons J Virol. 75:4226–38.
51. Nugent, C. I., K. L. Johnson, P. Sarnow, and K. Kirkegaard 1999. Functional coupling between replication and packaging of poliovirus replicon RNA J Virol. 73:427–35.
52. Olivo, P. D., P. L. Collins, M. E. Peeples, and S. Schlesinger 1998. Detection and quantitation of human respiratory syncytial virus (RSV) using minigenome cDNA and a Sindbis virus replicon: a prototype assay for negative-strand RNA viruses Virology. 251:198–205.
53. Olivo, P. D., I. Frolov, and S. Schlesinger 1994. A cell line that expresses a reporter gene in response to infection by Sindbis virus: a prototype for detection of positive strand RNA viruses Virology. 198:381–4.
54. Panda, S. K., I. H. Ansari, H. Durgapal, S. Agrawal, and S. Jameel 2000. The in vitro-synthesized RNA from a cDNA clone of hepatitis E virus is infectious J Virol. 74:2430–7.
55. Parsons, S. J., S. A. Rhodes, H. E. Connor, S. Rees, J. Brown, and H. Giles 2000. Use of a dual firefly and Renilla luciferase reporter gene assay to simultaneously determine drug selectivity at human corticotrophin releasing hormone 1 and 2 receptors Anal Biochem. 281:187–92.
56. Percy, N., W. S. Barclay, M. Sullivan, and J. W. Almond 1992. A poliovirus replicon containing the chloramphenicol acetyltransferase gene can be used to study the replication and encapsidation of poliovirus RNA J Virol. 66:5040–6.
57. Perri, S., D. A. Driver, J. P. Gardner, S. Sherrill, B. A. Belli, T. W. Dubensky, Jr., and J. M. Polo 2000. Replicon vectors derived from Sindbis virus and Semliki forest virus that establish persistent replication in host cells J Virol. 74:9802–7.
58. Pietschmann, T., V. Lohmann, G. Rutter, K. Kurpanek, and R. Bartenschlager 2001. Characterization of cell lines carrying self-replicating hepatitis C virus RNAs J Virol. 75:1252–64.
59. Podevin, P., A. Sabile, R. Gajardo, N. Delhem, A. Abadie, P. Y. Lozach, L. Beretta, and C. Brechot 2001. Expression of hepatitis C virus NS5A natural mutants in a hepatocytic cell line inhibits the antiviral effect of interferon in a PKR-independent manner Hepatology. 33:1503–11.
60. Polo, S., G. Ketner, R. Levis, and B. Falgout 1997. Infectious RNA transcripts from full-length dengue virus type 2 cDNA clones made in yeast J Virol. 71:5366–74.
61. Pugachev, K. V., M. S. Galinski, and T. K. Frey 2000. Infectious cDNA clone of the RA27/3 vaccine strain of Rubella virus Virology. 273:189–97.
62. Pur, B., S. Polo, C. G. Hayes, and B. Falgout 2000. Construction of a full length infectious clone for dengue-1 virus Western Pacific,74 strain Virus Genes. 20:57–63.

63. Racaniello, V. R. 1984. Studying poliovirus with infectious cloned cDNA Rev Infect Dis. 6 Suppl 2:S514–5.
64. Randhawa, J. S., A. C. Marriott, C. R. Pringle, and A. J. Easton 1997. Rescue of synthetic minireplicons establishes the absence of the NS1 and NS2 genes from avian pneumovirus J Virol. 71:9849–54.
65. Rice, C. M., A. Grakoui, R. Galler, and T. J. Chambers 1989. Transcription of infectious yellow fever RNA from full-length cDNA templates produced by in vitro ligation New Biol. 1:285–96.
66. Rice, C. M., R. Levis, J. H. Strauss, and H. V. Huang 1987. Production of infectious RNA transcripts from Sindbis virus cDNA clones: mapping of lethal mutations, rescue of a temperature-sensitive marker, and in vitro mutagenesis to generate defined mutants J Virol. 61:3809–19.
67. Roner, M. R., and W. K. Joklik 2001. Reovirus reverse genetics: Incorporation of the CAT gene into the reovirus genome Proc Natl Acad Sci USA. 98:8036–41.
68. Ryman, K. D., W. B. Klimstra, K. B. Nguyen, C. A. Biron, and R. E. Johnston 2000. Alpha/beta interferon protects adult mice from fatal Sindbis virus infection and is an important determinant of cell and tissue tropism J Virol. 74:3366–78.
69. Saito, S. 1990. Enhancement of the interferon-induced double-stranded RNA-dependent protein kinase activity by Sindbis virus infection and heat-shock stress Microbiol Immunol. 34:859–70.
70. Schlesinger, S., and T. W. Dubensky 1999. Alphavirus vectors for gene expression and vaccines Curr Opin Biotechnol. 10:434–9.
71. Schranz, P., H. Zentgraf, and C. H. Schroder 1990. Integrated defective replication units of hepatitis B virus Virus Genes. 4:367–74.
72. Sidhu, M. S., J. Chan, K. Kaelin, P. Spielhofer, F. Radecke, H. Schneider, M. Masurekar, P. C. Dowling, M. A. Billeter, and S. A. Udem 1995. Rescue of synthetic measles virus minireplicons: measles genomic termini direct efficient expression and propagation of a reporter gene Virology. 208:800–7.
73. Stanway, G., P. J. Hughes, G. D. Westrop, D. M. Evans, G. Dunn, P. D. Minor, G. C. Schild, and J. W. Almond 1986. Construction of poliovirus intertypic recombinants by use of cDNA J Virol. 57:1187–90.
74. Stewart, R. B., and E. T. Sheaff 1969. Effect of interferon on Sindbis virus growth in chick embryo cell cultures Can J Microbiol. 15:605–10.
75. Sudo, K., K. Konno, S. Shigeta, and T. Yokota 1996. Colorimetric assay system for screening antiviral compounds against hepatitis B virus Microbiol Immunol. 40:153–9.
76. Sumiyoshi, H., C. H. Hoke, and D. W. Trent 1992. Infectious Japanese encephalitis virus RNA can be synthesized from in vitro-ligated cDNA templates J Virol. 66:5425–31.
77. Tautz, N., T. Harada, A. Kaiser, G. Rinck, S. Behrens, and H. J. Thiel 1999. Establishment and characterization of cytopathogenic and noncytopathogenic pestivirus replicons J Virol. 73:9422–32.
78. van der Most, R. G., R. J. de Groot, and W. J. Spaan 1994. Subgenomic RNA synthesis directed by a synthetic defective interfering RNA of mouse hepatitis virus: a study of coronavirus transcription initiation J Virol. 68:3656–66.
79. Varnavski, A. N., and A. A. Khromykh 1999. Noncytopathic flavivirus replicon RNA-based system for expression and delivery of heterologous genes Virology. 255:366–75.
80. Varnavski, A. N., P. R. Young, and A. A. Khromykh 2000. Stable high-level expression of heterologous genes in vitro and in vivo by noncytopathic DNA-based Kunjin virus replicon vectors J Virol. 74:4394–403.
81. Vet, J. A., A. R. Majithia, S. A. Marras, S. Tyagi, S. Dube, B. J. Poiesz, and F. R. Kramer 1999. Multiplex detection of four pathogenic retroviruses using molecular beacons Proc Natl Acad Sci USA. 96:6394–9.
82. Volchkov, V. E., V. A. Volchkova, E. Muhlberger, L. V. Kolesnikova, M. Weik, 0. Dolnik, and H. D. Klenk 2001. Recovery of infectious Ebola virus from complementary DNA: RNA editing of the GP gene and viral cytotoxicity Science. 291:1965–9.
83. Wang, C. Y., G. Dominguez, and T. K. Frey 1994. Construction of rubella virus genome-length cDNA clones and synthesis of infectious RNA transcripts J Virol. 68:3550–7.
84. Weber, F., E. F. Dunn, A. Bridgen, and R. M. Elliott 2001. The Bunyamwera virus nonstructural protein NSs inhibits viral RNA synthesis in a minireplicon system Virology. 281:67–74.
85. Weiss, L., A. S. Kekule, U. Jakubowski, E. Burgelt, and P. H. Hofschneider 1996. The HBV-producing cell line HepG2-4A5: a new in vitro system for studying the regulation of HBV replication and for screening anti-hepatitis B virus drugs Virology. 216:214–8.
86. Whelan, S. P., L. A. Ball, J. N. Barr, and G. T. Wertz 1995. Efficient recovery of infectious vesicular stomatitis virus entirely from cDNA clones Proc Natl Acad Sci USA. 92:8388–92.
87. Widell, A., B. G. Hansson, B. Oberg, and E. Nordenfelt 1986. Influence of twenty potentially antiviral substances on in vitro multiplication of hepatitis A virus Antiviral Res. 6:103–12.
88. Wychowski, C., S. U. Emerson, J. Silver, and S. M. Feinstone 1990. Construction of recombinant DNA molecules by the use of a single stranded DNA generated by the polymerase chain reaction: its application to chimeric hepatitis A virus/poliovirus subgenomic cDNA Nucleic Acids Res. 18:913–8.
89. Zhang, F., Q. Huang, W. Ma, S. Jiang, Y. Fan, and H. Zhang 2001. Amplification and cloning of the full-length genome of Japanese encephalitis virus by a novel long RT-PCR protocol in a cosmid vector J Virol Methods. 96:171–82.

Primary screening programs to discover and identify compounds with antiviral activity can be designed in a variety of ways. All programs, however, fall into one of two general approaches. In the targeted approach, one particular biochemical target is chosen and candidate antiviral compounds are screened for inhibition of that target. The target is often an enzyme or a receptor that is known or thought to be essential to the process of viral replication. The alternative approach is unbiased such that inhibitors of viral replication are sought without a priori concern for the target. This unbiased approach generally involves use of cell culture since, as obligate intracellular pathogens, viruses can only replicate within cells. Although cell-based screening has been used successfully throughout the drug-discovery field, it is problematic when screening for antivirals. This is because it requires inoculation of infectious virus onto the cells and the production of additional infectious progeny virus. In particular, handling such infectious material is not easily compatible with the high throughput process of screening large libraries of compounds.

Thus, there is a need for improved methods and compositions that are useful for screening and analyzing antiviral compounds. In particular, these methods and compositions should be useful for high-throughput antiviral screening. The invention described herein satisfies that need.

SUMMARY OF THE INVENTION

Accordingly, the present invention provides methods and compositions utilizing subgenomic viral replication systems to evaluate potential antiviral compounds. The use of these methods and compositions allows rapid screening of the potential antiviral compounds against multiple viruses simultaneously.

In some embodiments, the present invention is directed to methods of screening a candidate antiviral agent for antiviral activity. The methods comprise the use of at least two subgenomic viral replication systems that are genetically distinct from each other. The methods involve preparing a first cell culture comprising cells containing a first subgenomic viral replication system, and a second cell culture comprising cells containing a second subgenomic viral replication system, adding the candidate antiviral agent to each cell culture, incubating the cell cultures under conditions and for a time sufficient to detect an antiviral effect by the candidate antiviral agent on the subgenomic viral replication systems, and determining the effect of the candidate antiviral agent on each viral replication system.

Related embodiments of the present invention are directed to methods of screening a candidate antiviral agent for antiviral activity. These methods also comprise the use of at least two subgenomic viral replication systems that are genetically distinct from each other. These methods include combining a first cell culture comprising cells containing a first subgenomic viral replication system and a second cell culture comprising cells containing a second subgenomic viral replication system to make a mixed cell culture, adding the candidate antiviral agent to the mixed cell culture, incubating the mixed cell culture under conditions and for a time sufficient to detect an antiviral effect by the candidate antiviral agent on the subgenomic viral replication systems, and determining the effect of the candidate antiviral agent on each viral replication system.

The present invention is also directed to mixed cell cultures that include a first cell culture comprising cells containing a first subgenomic viral replication system and a second cell culture comprising cells containing a second subgenomic viral replication system.

BRIEF DESCRIPTION OF THE DRAWINGS

FIG. 2 shows two graphs summarizing results from experiments demonstrating that yellow fever virus replicons cultured separately (top) have similar sensitivity to α-interferon as yellow fever virus replicons cultured with hepatitis C virus replicons and Sindbis virus replicons (bottom).

DETAILED DESCRIPTION OF THE INVENTION

Figure 1:
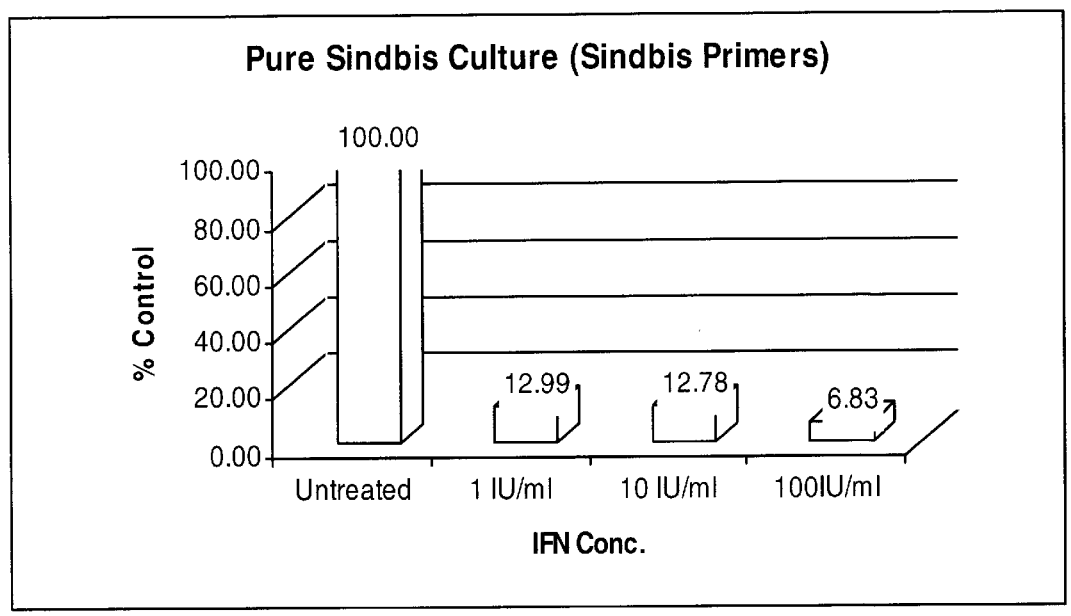
FIG. 1 shows two graphs summarizing results from experiments demonstrating that Sindbis virus replicons cultured separately (top) have similar sensitivity to α-interferon as Sindbis virus replicons cultured with hepatitis C virus replicons and yellow fever virus replicons (bottom).
Figure 1:
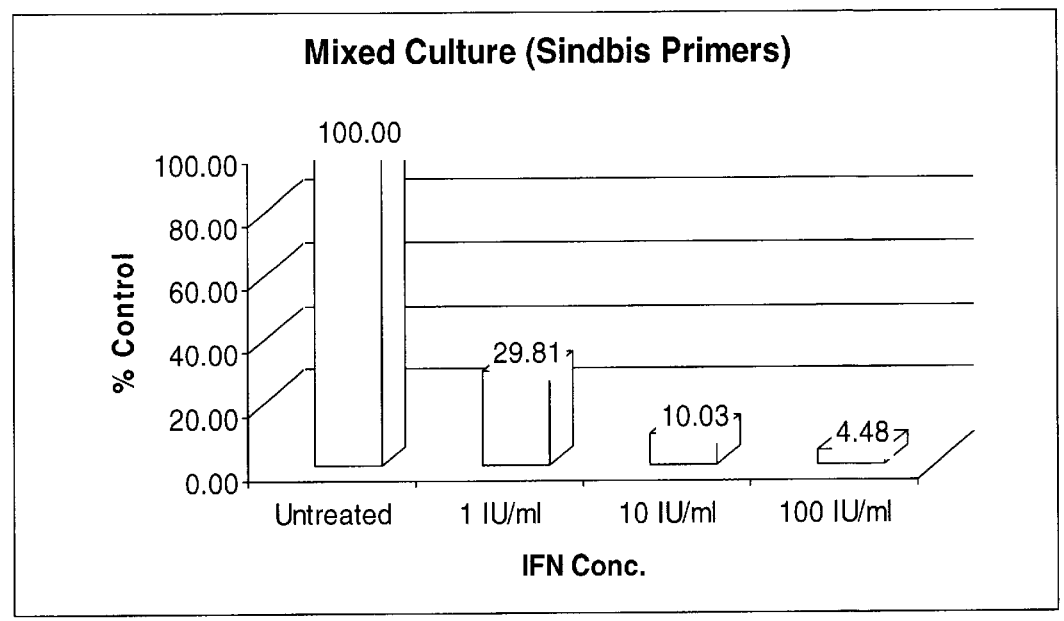

The present invention provides novel methods and compositions useful for evaluating candidate antiviral agents for antiviral activity. The methods comprise simultaneously evaluating the antiviral activity of the agent on more than one subgenomic viral replication system. In these methods, each subgenomic viral replication system is able to replicate in the cells of a cell culture so that the antiviral activity of the candidate antiviral agent is evaluated by applying the agent to the cell culture and determining the effect of the agent on replication of the subgenomic viral replication system in the cell culture.

As used herein, a subgenomic viral replication system is an incomplete viral genome capable of replication, but lacking in one or more genetic elements that are essential for producing infectious virus particles.

There are two types of subgenomic viral replication systems: replicons and defective genomes (minigenomes).

A viral replicon is a subgenomic viral replication system, derived from a viral genome, that is capable of replicating within cells cultured in vitro (Agapov et al., 1998). They typically encode all of the cis- and trans-acting viral components required for replication and transcription of the viral genome within a cell, but lack one or more functional element required for full virus replication. The element could be lacking due to a deletion of all or part of the sequence encoding that function, or the element could be lacking due to a mutation, such as a point mutation, rendering the element nonfunctional.

Recently several reports have described the selection of replicons capable of persistent replication in cells (Frolov et al., 1999). Thus, cell lines can be created that contain persistently replicating viral replicons for a number of viruses. Table 1 provides a partial list of viruses where replicons have been made or could be made without undue experimentation.

TABLE 1

Viral replicons for antiviral screening

| Family | Virus (common names) | Infectious clone | Noncytopathic replicon |
|---|---|---|---|
| Togaviridae | Sindbis | yes | yes |
| | Venezuela encephalitis virus | yes | possible |
| | Rubella | yes | possible |
| Picornaviridae | Poliovirus | yes | yes |
| | Coxsackirus | yes | possible |
| | Enterovirus | yes | possible |
| | Hepatitis A | yes | possible |
| Flaviviridae | Yellow fever | yes | yes |
| | Dengue fever | yes | possible |
| | West Nile virus | | possible |
| | Japanese Encephalitis virus | yes | yes |
| | Hepatitis C virus | yes | yes |
| | Tick-born encephalitis virus (TBE) | | possible |
| Astroviridae | Astrovirus | yes | possible |
| Rhabdoviridae | Rabies virus | yes | possible |
| Orthomyxoviridae | Influenza virus A | yes | possible |
| | Influenza virus B | | possible |
| Paramyxoviridae | Respiratory syncytial virus (RSV) | yes | possible |
| | Measles | yes | possible |
| | Mumps | yes | possible |
| Filoviridae | Ebola | yes | possible |
| | Marburg | | possible |
| Bunyaviridae | La Crosse virus | | possible |
| | California encephalitis virus | yes | possible |
| | Hantaan virus | | possible |
| | Crimean-Congo | | possible |
| | Rift Valley fever | | possible |

TABLE 1-continued

Viral replicons for antiviral screening

| Family | Virus (common names) | Infectious clone | Noncytopathic replicon |
|---|---|---|---|
| Arenaviridae | Lassa fever | | possible |
| | Argentine Hemorrhagic fever | | possible |
| | Bolivian Hemorrhagic fever | | possible |
| Reoviridae | Colorado tick fever | | |
| Hepadanviridae | Hepatitis B virus | yes | yes |
| Papillomaviridae | Human papilloma virus | yes | yes |
| Polyomaviridae | JC virus | yes | possible |
| | BK virus | yes | possible |
| Herpeviruses | Herpes simplex virus type one (HSV-1) | yes | yes |
| | Herpes simplex virus type two (HSV-2) | yes | possible |
| | Epstein-Barr virus (EBV) | yes | yes |
| | Human cytomegalovirus (HCMV) | yes | possible |
| | Varicella-zoster virus (VZV) | yes | possible |
| | Human herpes virus type six (HHV6) | possible | possible |
| | Human herpes virus type seven (HHV7) | possible | possible |
| | Human herpes virus type eight (HHV8) | possible | possible |
| Adenoviridae | Human adenovirus | yes | possible |
| Retrovirus | Human immunodeficiency virus type one (HIV-1) | yes | possible |
| | Human immunodeficiency virus type two (HIV-2) | yes | possible |
| | Human t-cell leukemia virus type one (HTLV-1) | yes | possible |
| | Human t-cell leukemia virus type two (HTLV-2) | yes | possible |
| Parvoviridae | Human parvovirus | yes | possible |
| | Adeno-associated virus | yes | yes |

Cell cultures comprising replicons offer a number of benefits in discovery and analysis of antiviral agents. They permit the effect of an antiviral agent to be observed in the context of living cells, so that any agents that show antiviral activity necessarily enter and act within living cells. Replicon-containing cell cultures also allow the immediate identification of antiviral agents with obvious undesirable cytotoxicity using well established cytotoxicity assays. These cell cultures also permit cell-based drug discovery screens and other studies to be performed against viruses such as hepatitis C virus (HCV) and human papillomavirus (HPV) that are unable to be conventionally cultured in vitro. Since viral functions related to infectivity are typically not required for viral genome replication, viral replicons lacking at least one infectivity-related sequence are much safer and thus easier to work with than infectious virus. As used herein, an infectivity-related sequence is a sequence required for the virus to infect a cell.

Another advantage of the replicon-containing cell cultures is that the replicons can be genetically manipulated to comprise heterologous sequences such as those encoding reporter genes such as luciferase, beta-galactosidase, secreted alkaline phosphatase or green fluorescent protein (MacDonald and Johnson, 2000) that facilitate high throughput automated analysis of viral genome copy number (Frolov et al., 1996).

An alternative approach to developing non-infectious viral replication systems is to use defective genomes. Defective viral genomes contain all the cis-acting elements required for viral genomic replication and transcription, but lack one or more of the genetic elements that encode the trans-acting factors required for replication. Such defective genomes, therefore cannot replicate by themselves (i.e. they are not replicons), but they can be replicated if the missing factor or factors are supplied in trans. A cell that contains the defective genome plus the necessary trans-acting factors exhibits a functional similarity to a replicon in that partial viral replication occurs within the cell and no infectious virus is produced. As with cell cultures containing replicating replicons, cell cultures containing replicating defective viral genomes represent a useful tool for antiviral drug discovery. Examples of defective genomes include the genomes contained within defective interfering virus particles that have been observed for many RNA and DNA viruses such as Alphaviruses (e..g. Sindbis virus) and herpesviruses (e.g. herpes simplex virus type one), respectively.

Another example of a defective genome is a minigenome. This is a type of artificial genome that has been constructed for a number of negative-strand RNA viruses such as respiratory syncytial virus (RSV), rabies virus, measles virus, etc. A minigenome of these viruses is an incomplete genome that contains all the cis-acting sequence elements that are required for replication of the viral RNA genome, but lack one or all of the coding regions of the complete viral genome.

Another example of defective viral genomes are so-called amplicons of DNA viruses such as herpesviruses (e.g. HSV-1), and other DNA viruses such as Papovaviruses (e.g. simian virus 40 (SV40). Such amplicons are circular DNA molecules that contain the viral origin(s) of replication and are replicated within cells by the trans-acting replication factors (origin-binding proteins, replication enzymes, etc.) required by the virus.

A screening process that utilizes these subgenomic viral replication systems can identify inhibitors of any biochemical pathway involved in viral genome replication and transcription of viral genes. One need only select a screening procedure that evaluates the effects on the pathway of interest to be able to measure the effects of a candidate antiviral agent on that pathway. For example, to identify an agent that targets any pathway involved in replication, an end product of replication (for example the replicated genome) is measured after treatment with the agent by, e.g., performing quantitative PCR to quantify the amount of a representative portion of the genome that is present. Alternatively, to identify an agent that targets a specific pathway involved in replication, e.g., translation of RNA polymerase, one could measure that particular component, e.g. quantifying RNA polymerase by an antibody assay.

The present invention provides methods and compositions for utilizing the advantages of subgenomic viral replication systems to screen candidate antiviral agents against multiple viruses simultaneously. By treating more than one subgenomic viral replication system with a candidate antiviral agent at the same time, candidate agents can be screened more rapidly. This multiple treatment approach also provides the ability to compare the effects of a candidate antiviral agent on each tested virus simultaneously. Thus, this system provides information on the specificity of the antiviral effect. This information is helpful, for example, in assessing whether the effect is acting on a specific viral target or on a cellular target and thus exerting its effect on the virus(es) indirectly. In addition this approach allows for the identification of compounds which exhibit broad antiviral activity and thus could be effective against many viruses.

In preferred embodiments of the invention, the cell cultures harboring subgenomic viral replication systems are combined into a multiple subgenomic replication culture (MSRC) also referred to as a mixed viral replicon culture (MVRC). This is possible because the replicons and minigenomes useful for the invention do not spread from cell to cell. Thus, each cell can be considered to be an autonomous unit, and determination of the effect of a candidate antiviral agent on each virus only requires that the various subgenomic viral replicon systems be distinguishable, e.g., by PCR methods or any other method that is capable of only amplifying a fragment of one of the subgenomic replication systems.

An MSRC offers a screening system in antiviral drug discovery that provides additional and distinct advantages over the use of cultures that only contain one subgenomic replication system. One advantage of using an MSRC for screening candidate antiviral agents is that it reduces the cost and labor required to analyze the effects of a large panel of candidate agents on sets of distinct viruses. Another advantage of using an MSRC is that it simplifies the comparison of drug effects on distinct viral replicons as it insures that all replicons were exposed to the same quantity of compound under the same culture conditions.

Another advantage of using an MSRC for antiviral screening is that an MSRC system permits detection of antivirals that would be overlooked in a single virus screening system. In standard single-virus screening systems where antiviral agents affecting a single virus are generally identified by an antiviral effect above a threshold inhibition level. In those procedures, antiviral agents with sub-threshold levels of activity against the screened viral target are discarded. By screening a MSRC system, both specific inhibitors that target any one of the multiple targets and broad-spectrum agents that effect multiple viruses can be identified. Simultaneous recovery of inhibition data for a variety of distinct viral replicons thus permits identification of antiviral agents that might otherwise be overlooked.

Although the creation, analysis, and advantages of using MSRCs in antiviral drug discovery have not been described, multiplexed viral detection assays that permit quantification of multiple viruses in a single sample are known and used primarily for diagnosis of viral infections. For example, quantitative reverse transcription-polymerase chain reaction (qRT-PCR) mediated detection assays for multiple viruses in a single sample have been described (Elnifro et al., 2000; Grondahl et al., 1999; Fan et al., 1998; Jungkind et al., 1996; Burgart et al., 1992). Molecular beacon-based hybridization probes have also been employed to detect multiple viruses in a single sample (Vet et al., 1999). Multiplex assays for distinct gene reporters that can be independently assayed from the contents of a single culture well have also been described (Parsons et al, 2000; Grentzmann et al, 1998). While multiplexed viral detection assays may facilitate analysis of the effect of a candidate antiviral agent on an MSRC, they do not anticipate MSRCs or make them obvious, or teach how to develop antiviral screening methods using MSRCs, because they do not utilize the advantages afforded with subgenomic viral replication systems. Additionally, the multiplex assays previously described are also not required to practice the antiviral screening assays of the present invention which utilize MSRCs, since schemes for subdividing the contents of an MSRC into multiple single well assays can be easily devised.

Thus, in some embodiments, the present invention is directed to methods of screening a candidate antiviral agent for antiviral activity. The methods comprise the following steps:

(a) preparing a first cell culture comprising cells containing a first subgenomic viral replication system, and a second cell culture comprising cells containing a second subgenomic viral replication system;

(b) adding the candidate antiviral agent to each cell culture;

(c) incubating the cell cultures under conditions and for a time sufficient to detect an antiviral effect by the candidate antiviral agent on the subgenomic viral replication systems; and (d) determining the effect of the candidate antiviral agent on each viral replication system.

Although some advantages are achieved from this invention even if the cells containing the subgenomic viral replication systems are separate while performing the method, it is preferred that the cultures are mixed together into an MSRC prior to step (b). In those embodiments, the MSRC can contain from two to ten or more subgenomic viral replication systems, provided the effect of the candidate antiviral agent on each individual subgenomic viral replication system can be discerned. It is also possible to have more than one subgenomic viral replication system in a cell (see Example 2).

Thus, since each cell is an independent unit harboring a subgenomic viral replication system, each cell can be considered to potentially provide independent information relating to the candidate antiviral agent. Therefore, the number of different subgenomic viral replication systems that can be combined in an MSRC can be as high as the number of cells in the MSRC, provided methods to evaluate viral replication in each cell are available. An example of such a method is the provision of different reporter genes with each subgenomic viral replication system where each reporter gene, for example, provides a different fluorescent end product (using e.g., molecular beacons specific for each viral RNA, or different fluorescent proteins and/or fluorescent products of an enzyme encoded by the subgenomic viral replication system). Each cell can then be analyzed by quantifying the intensity of the fluorescence of the fluorescent moiety associated with the subgenomic viral replication system in that cell. Optionally, such data can be obtained from each cell, e.g. using a fluorescence activated cell sorter.

The MSRC can also comprise a control cell culture which does not contain a subgenomic viral replication system in order to directly measure the effect of the candidate antiviral agent on the cells themselves.

The cells useful for this invention are any cells that can be grown in culture and that are capable of harboring a subgenomic viral replication system. This would include cells from any eukaryotic family, including plants, fungi, insects, and protists. In most embodiments, the cells will be from the same organism that is capable of harboring the virus of interest. In preferred embodiments, the cells are animal cells, preferably mammalian cells; in most preferred embodiments, the cells are human cells.

The cells useful for these methods can be either primary cells or from an established cell line. When grown together in a MSRC, the cells must have similar growth conditions such that each cell will support replication of the subgenomic viral replication system that it contains.

The subgenomic viral replication system in the cells can be transient or stably maintained in the cells. It is only required that the subgenomic viral replication system be able to replicate for sufficient time to be able to evaluate whether replication is inhibited by the candidate antiviral agent.

Each subgenomic viral replication system used in the methods and compositions of the present invention must be genetically distinct from the other subgenomic viral replication system(s) evaluated. The subgenomic viral replication systems can be in different virus families or same family, they can be the same virus but different genotypes, or even different mutants of same virus. The only requirement is that they must be distinguishable from each other in the embodiments where the two cell cultures are mixed together. In some embodiments, the subgenomic viral replication systems can differ by as little as one basepair. Such a method could be useful, for example, in determining whether a particular protein that is mutated in one subgenomic viral replication system, but not the other system, is the target of the candidate antiviral agent.

The methods of the present invention are useful for any virus that can be made into a subgenomic viral replication system, including DNA viruses, RNA viruses, retroviruses and viroids. It is also envisioned that the invention methods would be adaptable for any virus that cannot now be made into a subgenomic viral replication system but could be made into such a system in the future.

The viruses useful for this invention includes any virus from which a subgenomic viral replication system can be derived. This would include viruses that infect the cells of organism from any eukaryotic kingdom, phyla, or family, including plants, fungi, insects, and protists. In preferred embodiments, the virus infects animal cells, preferably mammalian cells; in most preferred embodiments, the virus infects human cells. Examples of preferred viruses are included in Table 1, and include hepatitis C virus, yellow fever virus, respiratory syncytia virus and Sindbis virus, as utilized in the Examples.

Any candidate antiviral agent can be evaluated using the methods of the present invention, including any small to large organic or inorganic molecule, provided the agent can be taken up by the cells when added to the culture. To assist in this uptake, the candidate antiviral agent can be formulated into compositions comprising excipients such as liposomes, amphipathic compounds etc., as is well known in the art. The cells harboring the subgenomic viral replication system can also be treated, e.g., with polyethylene glycol or with an electroporation device, to assist in the uptake of the candidate antiviral agent.

Nonlimiting examples of candidate antiviral agents include nucleotides or nucleosides (e.g., AZT); oligonucleotides or polynucleotides such as antisense compounds, vectors comprising antisense or genes encoding antiviral proteins, including plasmids, viral vectors, etc. Nucleic acid mimics such as peptide nucleic acids (see, e.g., Corey, 1997), and other nucleic acid binding compounds, (e.g., those described in Geierstanger et al., 1996) can also be utilized as candidate antiviral agents. Additionally, secondary metabolites and other small chemicals, bioactive amino acids, oligopeptides or polypeptides can be tested for antiviral activity, including antibodies and compounds comprising antibody binding sites, enzymes, structural proteins, growth factors, transcription factors, etc.

After adding the candidate antiviral agent to the cell culture, the cells are incubated under conditions and for a time sufficient to detect an antiviral effect by the agent. Depending on the virus, what is being measured to evaluate antiviral activity, and the nature of the cells harboring the subgenomic viral replication system, the optimum time of incubation could be anywhere from 1 minute to 48 hours, or longer. The shorter time periods are envisioned, for example, where the antiviral activity of the candidate antiviral agent is measured by evaluating whether the agent binds to, e.g., a particular protein, such as an enzyme, where inhibition of enzyme activity, or binding of the candidate agent to the enzyme, is measured.

When the antiviral activity of the candidate antiviral agent is measured by determining whether replication has been inhibited by the agent, the cell culture must be incubated long enough to allow a measurable amount of replication to occur, but not so long that the cells overgrow the culture dish. With virus/cell combinations such as those used in the Examples below (hepatitis C virus replicon in Huh7 hepatocytes; Sindbis virus replicon in BHK kidney fibroblasts; yellow fever virus replicon in Huh7 cells; respiratory syncytia virus minigenome transiently expressed in the above-described BHK cells harboring the Sindbis replicon), 20–24 hours incubation was determined to be optimum.

In some aspects of the invention, the antiviral effect of the candidate antiviral agent is determined by an assessment of the amount of replication that has occurred. Nonlimiting examples of methods for making these determinations include any method of RNA or DNA quantitation that involves target amplification, such as quantitative RT-PCR or PCR or transcription mediated amplification; or non-amplification DNA or RNA quantitation methods, particularly those that involve signal amplification such as branched chain DNA, but also northern or Southern hybridization, in-situ hybridization, molecular beacons, etc. To ascribe copy numbers of replicon, comparison with RNA standards can be made.

For any particular subgenomic viral replication system, the appropriate assay to measure viral replication would be within the ability of a skilled artisan to determine without undue experimentation.

The activity of a candidate antiviral agent can also be determined by methods that target a particular component of the virus required for replication. Such assays might be desirable, for example, if the candidate antiviral agent was an antisense oligonucleotide that binds to a gene encoding a protein such as an enzyme essential for viral replication. For these targeted assays, any method for quantitation of the specific protein could be useful, for example immunoassays such as EIA, ELISA, immunoblotting, immunofluorescence or immunoprecipitation; assays for enzymatic activity of a particular viral enzyme, for example RNA or DNA polymerase, protease, helicase, thymidine kinase, ribonucleotide reductase, etc.; or assays of products of reporter genes that have been fused to a particular viral protein or otherwise inserted into the genome. Nonlimiting examples of these reporter proteins include luciferase, green fluorescent protein, and β-galactosidase.

In other embodiments, the present invention is directed to mixed cell cultures comprising a first cell culture comprising cells containing a first subgenomic viral replication system and a second cell culture comprising cells containing a second subgenomic viral replication system. These were previously named multiple subgenomic replication cultures or MSRCs. Any of the mixed cell cultures that are useful for the methods of screening candidate antiviral agents as described above are envisioned to be within the scope of these embodiments. Included are mixed cell cultures harboring any number of subgenomic viral replication systems up to the number of cells in the culture, for example three, four, five, ten, twenty or more independent subgenomic viral replication systems.

Preferred embodiments of the invention are described in the following Examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

Multiplex Screening of HCV/YFR/SINDBIS in Mixed Viral Replicon Culture

To determine if the effects of well characterized antiviral agents could be observed in an MVRC, cell lines containing HCV, yellow fever, and Sindbis viral replicons were cultured both independently and as mixed cultures in the presence and absence of fixed amounts of α-interferon (IFNα), a well characterized antiviral agent (Constantinescu, 1991). Interferon has previously been shown to inhibit replication of HCV both in vivo and in vitro (Podevin et al, 2001; Stewart and Sheaff, 1969; Ryman et al., 2000; Saito, 1990; Arroyo et al., 1988). Following exposure to the antiviral agent, RNA was extracted from the cells and the levels of viral replicon determined via a qRT-PCR assay.

Materials and Methods

Viral Replicon Cultures. The Sindbis viral replicon system referred to as BHK/SR19/pac and the HCV replicon Ava.5 cell lines were generated as described previously (Frolov et al., 1999; Blight et al., 2000; Bredenbeek et al., 1993; Rice et al, 1987). The yellow fever virus (YFR) replicon-containing Huh7 cells were made using a similar strategy (Rice et al., 1989).

Cells were seeded in standard 12-well microtiter dishes (appx. 5 cm$^2$) with the indicated levels of the antiviral agents α-interferon (Sigma, St. Louis, Mo.) in minimal essential media (MEM, Life Technologies, Gaithesburg, Md.) plus 10% fetal bovine serum and incubated at 37° C. under standard conditions. The total number of cells seeded to each well was 200,000. When the three cultures were mixed, the relative proportions of each were 30% HCV/40% Sindbis/30% YFR replicon containing cells.

qRT-PCR Analysis. RNA from the cell cultures was prepared via a commercially available kit (RNAeasyJ, Qiagen, Valencia, Calif.). RNA was subsequently added to a qRT-PCR aqueous cocktail (50 μL) consisting of 10 μL 5× EZ Buffer, 25 μL 10×manganese acetate, 3 μL of each primer at 5 μM, 1.5 μL of each dNTP at 10 mM; 0.5 μL of uracil-N-glycosylase (as supplied); 2.0 μL of rTth Polymerase (2.5 u/1 μL) (EZ rTth RNA PCR Kit, Perkin Elmer, Boston, Mass.) and 5 uL of a 1:10,000 dilution of SYBR GreenJ Fluorescent Dye as supplied (SYBR GreenJ, Molecular Probes, Eugene, Oreg.).

Primers for amplification of the HCV 3' NTR sequence are: 5'-ggctccatcttagccctagtc (SEQ ID NO:1) and 3'-agtatcggcactctctgcagt (SEQ ID NO:2). The YFR replicon was identified by the primers: 5'-ggatgcaggtaccactagaa (SEQ ID NO:3) and 3'-cgtggtggatctggttgatt (SEQ ID NO:4). The Sindbis replicon was identified by the primers: 5'-gagagcgccacgttagtgta (SEQ ID NO:5) and 3'-accttgtactgctcctcttc (SEQ ID NO:6).

Real time fluorescence monitoring of the qRT-PCR reaction was accomplished and assignment of the threshold PCR amplification cycle (i.e. the thermal reaction cycle at which detectable exponential amplification of the reaction product is observed) via use of a BioRad I-cycler instrument. Experiments with dilutions of RNA target standards at known concentrations confirm that the threshold cycle is an accurate measure of viral replicon levels. The threshold cycle value for the no interferon control was arbitrarily set to 100% (i.e. 100% of control) with values in the presence of interferon expressed as a percentage of the negative control.

Results

Figure 3:
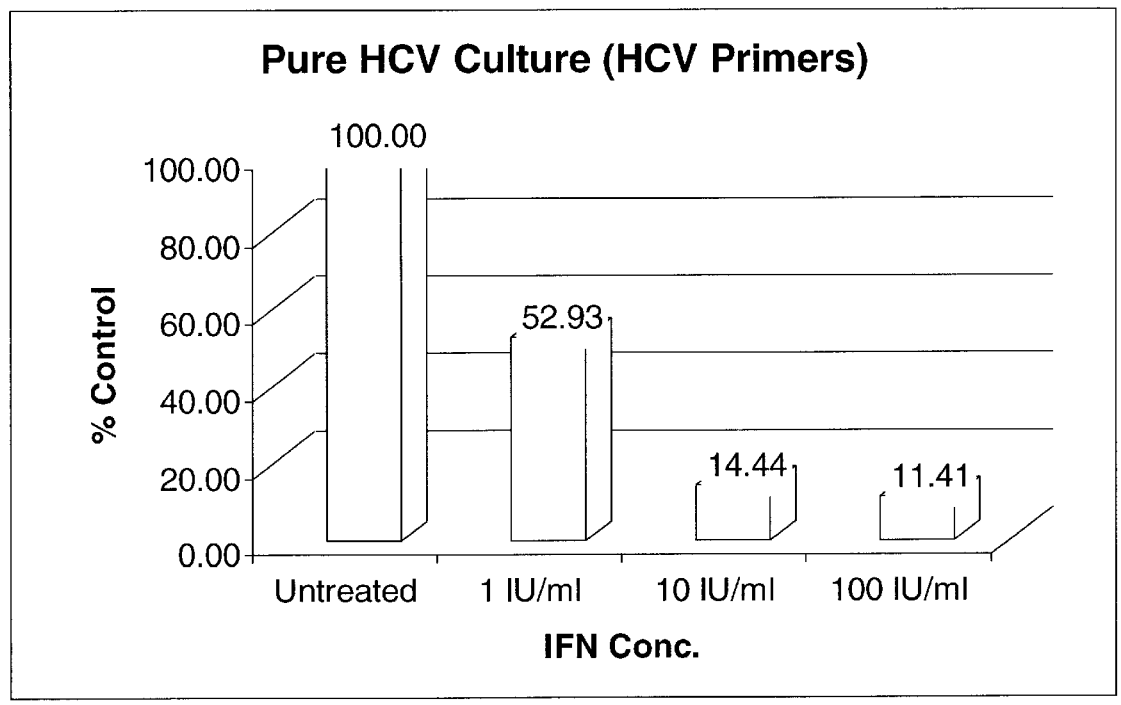
FIG. 3 shows two graphs summarizing results from experiments demonstrating that hepatitis C virus replicons cultured separately (top) have similar sensitiity to α-interferon as hepatitis C virus replicons cultured with Sindbis virus replicons and yellow fever virus replicons (bottom).
Figure 3:
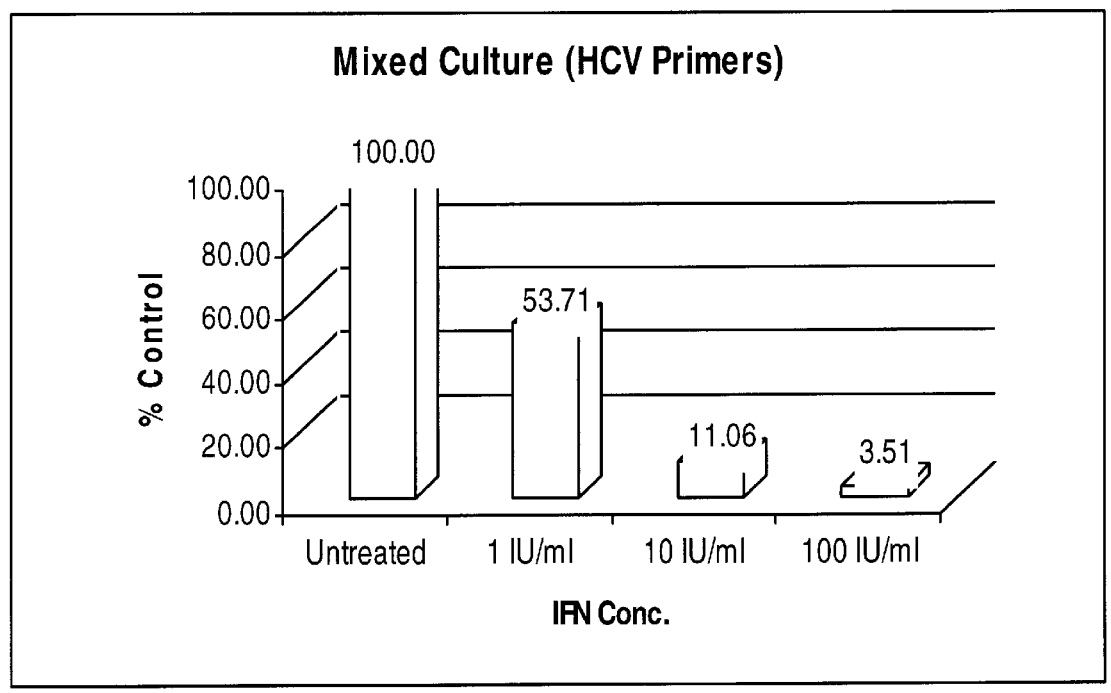

Table 2 shows the results of an experiment using real time quantitative polymerase chain reaction (qRT-PCR) to measure the effect of IFNα on three viral replicons assayed in a mixed viral replicon culture. Since each replicon-containing cells were all exposed to IFNα under exactly the same conditions, the relative effect of IFNα on distinct replicons is easily determined. In this example it is readily apparent that the inhibitory effects of IFNα are most pronounced in Sindbis (>98% inhibition at 100 u/ml IFNα), followed by HCV (>91% at 100 u/ml) and YFR (>81% at 100 u/ml). These results are very similar to the effect of IFNα on each viral replicon when cultured separately (FIGS. 1, 2 and 3).

When ribavirin was tested in the mixed cultures, no effect was observed on HCV replication, even at the highest concentration tested (100 μg/ml) (Table 3). However, ribavirin did inhibit Sindbis replicon replication in the mixed cultures. This further shows that antiviral agents act independently on the various subgenomic viral replication systems in multiple subgenomic replication cultures.

TABLE 2

Levels of replicon RNA of co-cultured hepatitis C virus (HCV), Sindbis virus, and yellow fever virus replicons following α-interferon (IFNα) treatment.

| IFNα (Units/ml) | HCV Mixed Viral Replicon Culture % of Control (ave) | % CV | Sindbis Mixed Viral Replicon Culture % of Control (ave) | % CV | YFR Mixed Viral Replicon Culture % of Control (ave) | % CV |
|---|---|---|---|---|---|---|
| 0 | 100.00 | 31.06 | 100.00 | 38.47 | 100.00 | 43.67 |
| 1 | 28.10 | 10.50 | 14.88 | 5.39 | 41.47 | 24.17 |
| 10 | 14.94 | 5.92 | 8.53 | 4.41 | 26.09 | 12.95 |
| 100 | 8.43 | 1.95 | 1.49 | 0.22 | 18.64 | 13.19 |

TABLE 3

Comparison of ribivirin and interferon effects on HCV and Sindbis replicon replication in mixed viral replicon culture.

| Ribavirin (μg/ml) | HCV Mixed Viral Replicon Culture % of Control (ave) | % CV | Sindbis Mixed Viral Replicon Culture % of Control (ave) | % CV |
|---|---|---|---|---|
| 0 | 100.00 | 4.55 | 100.00 | 11.23 |
| 0.5 | 100.37 | 6.50 | 40.54 | 8.20 |
| 1 | 101.51 | 5.34 | 62.98 | 12.34 |
| 10 | 99.75 | 5.56 | 35.04 | 8.04 |
| 100 | 110.22 | 3.76 | 18.11 | 1.28 |
| IFN-α (Units/ml) | | | | |
| 0 | 100.00 | 35.04 | 100.00 | 12.81 |
| 100 | 4.59 | 1.89 | 47.58 | 14.34 |
| 1000 | 1.74 | 0.10 | 16.22 | 3.80 |

EXAMPLE 2

Multiplex Screening of Stable and Transient Viral Replicons: HCV/RSV/Sindbis in Mixed Culture In Example 1, the feasibility of assaying multiple viral replicons cultured in a single well was demonstrated. Each of the viral replicons analyzed in the Example 1 is capable of autonomous replication within a cell line where it is stably maintained. However, there are other subgenomic viral replication systems that are not stably maintained. These systems require the use of a transient cell culture where the viral genome is introduced into the cells via transfection or electroporation. Once introduced, these transient replicons or minigenomes will display viral protein-mediated subgenomic replication for a limited time before cells lacking viral sequences proliferate and predominate within the culture. There is clear value in being able to analyze the effect of antiviral agents on transient replicon or minigenome systems since stable viral replicon or minigenome systems have yet to be established for certain viruses.

Respiratory syncytia virus (RSV) is one example of a virus for which only a transient minigenome system is currently available. To determine if a multiple subgenomic replication culture containing both stable and transient subgenomic viral replication systems could be used to assay the effects of antiviral agents, stable HCV replicon-containing cells were mixed with cells containing a stable Sindbis replicon that had been transfected with a transient RSV minigenome system. This multiple subgenomic replication culture was subjected to both ribavirin and α-interferon treatment followed by qRT-PCR analysis of replicon/minigenome levels.

Materials and Methods

Viral Cultures.

The Sindbis viral replicon system referred to as BHK/SR19/T7/pac and the HCV replicon Ava.5 cell lines were generated as described previously. The RSV minigenome system consisted of the following five plasmids: C2-LUC RSV minigenome cDNA (Collins et al, 1996); pTM1-N, pTM1-P, pTM1-L (Grosfeld et al, 1995); and pM2-1. The pM2-1 vector was constructed by amplifying RSV (strain 2) M2-1 cDNA by reverse transcription PCR (RT-PCR) with the primers ccaaggatatttgtcagg (SEQ ID NO:7) and ggggcaaatatgtcacgaaggaatcc (SEQ ID NO:8). The PCR product was cloned into pCR-Blunt (Invitrogen), cut out with EcoRI and cloned into the EcoRI site of the T7 expression vector pMH4. The pMH4 expression vector was derived from pTM1 (Elroy-Stein et al., 1989; kindly provided by Bernhard Moss, National Institutes of Health) by removal of the NcoI site.

To generate the cell line BHK/SR19/T7/pac/C2-LUC that transiently expresses the RSV minigenome C2-LUC, 3×10$^6$ BHK/SR19/T7/pac cells were seeded into 10 cm$^2$ dishes. After 16 h the cells were transfected with 6 μg of C2-LUC, 1.2 μg pTM1-N, 0.6 μg pTM1-P, 1.2 μg pTM1-L and 0.6 μg pMH4-M2-1 per 10 cm$^2$ dish using the transfection reagent lipofectamine (Gibco Invitrogen, Carlsbad, Calif.). After 5–6 h the transfection media was replaced with new growth media. 16 h post transfection the cells were trypsinized, counted and seeded into a 96 well plate at 8×10$^3$ cells/well for each of the two cell lines. BHK/SR19/T7/pac/C2-LUC, BHK/SR19/T7/pac and Ava.5 cells were seeded at 8×10$^3$ cells/well and served as control groups. All cell groups were set up in the presence of various concentrations of ribavirin or α-interferon. After 24 h the cells were harvested for RNA extraction, qRT-PCR analysis was as in Example 1.

Results

As with the stable replicons (HCV, YFR and Sindbis), RSV transient minigenome cell cultures showed similar sensitivity to ribovirin and α-interferon whether in a single viral culture or a mixed culture (Table 4).

TABLE 4

Comparison of ribavirin and α-interferon (IFN-α) effects on RSV minigenome replication in mixed and single viral replicon culture.

| Ribavirin (μ/ml) | RSV Mixed Viral Culture % of Control (ave) | % CV | RSV Single Viral Culture % of Control (ave) | % CV |
|---|---|---|---|---|
| 0 | 100.00 | 43.21 | 100.00 | 28.72 |
| 0.5 | 96.16 | 39.35 | 97.31 | 8.30 |
| 1 | 44.14 | 12.68 | 17.86 | 3.93 |
| 10 | 42.42 | 14.55 | 3.74 | 0.18 |
| 100 | 13.90 | 5.07 | 2.82 | 0.53 |

TABLE 4-continued

Comparison of ribavirin and α-interferon (IFN-α) effects on RSV minigenome replication in mixed and single viral replicon culture.

| Ribavirin (μ/ml) | RSV Mixed Viral Culture % of Control (ave) | % CV | RSV Single Viral Culture % of Control (ave) | % CV |
|---|---|---|---|---|
| IFN-α (Units/ml) | | | | |
| 0 | 100.00 | 13.21 | 100.00 | 13.21 |
| 100 | 84.30 | 33.61 | 84.30 | 34.02 |
| 1000 | 77.80 | 56.54 | 47.29 | 7.47 |

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

SEQ ID Nos—

SEQ ID NO:1
HCV 3' NTR 5' primer CB3N51
ggctccatcttagccctagtc

SEQ ID NO:2
HCV 3' NTR 3' primer CM38B5
agtatcggcactctctgcagt

SEQ ID NO:3
YFR 5' primer 2535
ggatgcaggtaccactagaa

SEQ ID NO:4
YFR 3' primer 2638
cgtggtggatctggttgatt

SEQ ID NO:5
Sindbis 5' primer SV1938
gagagcgccacgttagtgta

SEQ ID NO:6
Sindbis 3' primer SV2044
accttgtactgctcctcttc

SEQ ID NO:7
RSV M2-1 cloning primer 1
ccaaggatatttgtcagg

SEQ ID NO:8
RSV M2-1 cloning primer 2
ggggcaaatatgtcacgaaggaatcc

SEQ ID NO:9
luciferase 5' primer
catcacgtacgcggaatact

SEQ ID NO:10
luciferase 3' primer
cgcaactgcaactccgataa

What is claimed is:

1. A method of screening a candidate antiviral agent for antiviral activity comprising
 (a) preparing a first cell culture comprising cells containing a first subgenomic viral replication system, and a second cell culture comprising cells containing a second subgenomic viral replication system; then
 (b) adding the candidate antiviral agent to each cell culture; then
 (c) incubating the cell cultures under conditions and for a time sufficient to detect an antiviral effect by the candidate antiviral agent on the subgenomic viral replication systems; and
 (d) determining the effect of the candidate antiviral agent on each viral replication system,
 wherein the first subgenomic viral replication system is genetically distinct from the second subgenomic viral replication system, and wherein the first and second cell cultures are combined before step (b).

2. The method of claim 1, further comprising, in step (a), preparing a third cell culture comprising cells not containing a subgenomic viral replication system.

3. The method of claim 1, wherein at least one of the subgenomic viral replication systems is a replicon.

4. The method of claim 1, wherein at least one of the subgenomic viral replication systems is a defective genome.

5. The method of claim 1, wherein the cells in the first and second cell cultures are mammalian cells and the first and second subgenomic viral replication systems are from mammalian viruses.

6. The method of claim 5, wherein the mammalian cells are human cells and the mammalian viruses are human viruses.

7. The method of claim 6, wherein the human viruses are selected from the group consisting of hepatitis C virus, yellow fever virus, respiratory syncytial virus, Sindbis virus, poliovirus, Japanese encephalitis virus, hepatitis B virus, human papilloma virus, herpes simplex virus type 1, Epstein-Barr virus, adeno-associated virus, Venezuela encephalitis virus, rubella, coxsackevirus, enterovirus, hepatitis A virus, Dengue fever virus, West Nile virus, tick-borne encephalitis virus, astrovirus, rabies virus, influenza virus A, influenza virus B, measles, mumps, Ebola virus, Marburg virus, La Crosse virus, California encephalitis virus, Hantaan virus, Crimean-Congo virus, Rift Valley fever, Lassa fever, Argentine hemorrhagic fever virus, Bolivian hemorrhagic fever virus, Colorado tick fever, JC virus, BK virus, herpes simplex virus type two, human cytomegalovirus, varicella-zoster virus, human herpes simplex virus type six, human herpes virus type seven, human herpes virus type eight, human adenovirus, HIV-1, HIV-2, HTLV-1, HTLV-2, and human parovirus.

8. The method of claim 6, wherein the human viruses are selected from the group consisting of hepatitis C virus, yellow fever virus, respiratory syncytial virus, Sindbis virus, poliovirus, Japanese encephalitis virus, hepatitis B virus, human papilloma virus, herpes simplex virus type 1, Epstein-Barr virus, and adeno-associated virus.

9. The method of claim 6, wherein the human viruses are selected from the group consisting of hepatitis C virus, respiratory syncytial virus, yellow fever virus and Sindbis virus.

10. The method of claim 1, further comprising at least a third cell culture comprising cells containing a third subgenomic viral replication system, wherein the third cell culture is also subjected to steps (a), (b), (c) and (d),
 wherein each subgenomic viral replication system is genetically distinct from every other subgenomic viral replication system.

11. The method of claim 10, wherein all cell cultures comprising a subgenomic viral replication system are combined before step (b).

12. A mixed cell culture comprising a first cell culture comprising cells containing a first subgenomic viral replication system and a second cell culture comprising cells containing a second subgenomic viral replication system.

13. The mixed cell culture of claim 12, wherein at least one of the subgenomic viral replication systems is a replicon.

14. The mixed cell culture of claim 12, wherein at least one of the subgenomic viral replication systems is a defective genome.

15. The mixed cell culture of claim 12, wherein all of the cells of the mixed cell culture are the same cell line.

16. The mixed cell culture of claim 12, wherein the cells of the mixed cell culture comprise more than one cell line.

17. The mixed cell culture of claim 12, wherein all of the cells in the mixed cell culture are mammalian cells and all of the subgenomic viral replication systems are from mammalian viruses.

18. The mixed cell culture of claim 17, wherein the mammalian cells are human cells and the mammalian viruses are human viruses.

19. The mixed cell culture of claim 18, wherein the human viruses are selected from the group consisting of hepatitis C virus, yellow fever virus, respiratory syncytial virus, Sindbis virus, poliovirus, Japanese encephalitis virus, hepatitis B virus, human papilloma virus, herpes simplex virus type 1, Epstein-Barr virus, adeno-associated virus, Venezuela encephalitis virus, rubella, coxsackievirus, enterovirus, hepatitis A virus, Dengue fever virus, West Nile virus, tick-borne encephalitis virus, astrovirus, rabies virus, influenza virus A, influenza virus B, measles, mumps, Ebola virus, Marburg virus, La Crosse virus, California encephalitis virus, Hantaan virus, Crimean-Congo virus, Rift Valley fever, Lassa fever, Argentine hemorrhagic fever virus, Bolivian hemorrhagic fever virus, Colorado tick fever, JC virus, BK virus, herpes simplex virus type two, human cytomegalovirus, varicella-zoster virus, human herpes simplex virus type six, human herpes virus type seven, human herpes virus type eight, human adenovirus, HIV-1, HIV-2, HTLV-1, HTLV-2, and human parvovirus.

20. The mixed cell culture of claim 18, wherein the human viruses are selected from the group consisting of hepatitis C virus, yellow fever virus, respiratory syncytial virus, Sindbis virus, poliovirus, Japanese encephalitis virus, hepatitis B virus, human papilloma virus, herpes simplex virus type 1, Epstein-Barr virus, and adeno-associated virus.

21. The mixed cell culture of claim 18, wherein the human viruses are selected from the group consisting of hepatitis C virus, respiratory syncytial virus, yellow fever virus and Sindbis virus.

22. The mixed cell culture of claim 12, further comprising a third cell culture comprising cells containing a third subgenomic viral replication system.

23. The mixed cell culture of claim 22, wherein the mixed cell culture further comprises a fourth cell culture comprising cells containing a fourth subgenomic viral replication system.

* * * * *

SEQUENCE LISTING

<160> NUMBER OF SEQ ID NOS: 10

<210> SEQ ID NO 1
<211> LENGTH: 21
<212> TYPE: DNA
<213> ORGANISM: Hepatitis C virus 3' NTR 5' primer CB3N51

<400> SEQUENCE: 1
ggctccatct tagccctagt c                                          21

<210> SEQ ID NO 2
<211> LENGTH: 21
<212> TYPE: DNA
<213> ORGANISM: Hepatitis C virus 3' NTR 3' primer CM38B5

<400> SEQUENCE: 2
agtatcggca ctctctgcag t                                          21

<210> SEQ ID NO 3
<211> LENGTH: 20
<212> TYPE: DNA
<213> ORGANISM: Yellow fever virus 5' primer 2535

<400> SEQUENCE: 3
ggatgcaggt accactagaa                                            20

<210> SEQ ID NO 4
<211> LENGTH: 20
<212> TYPE: DNA
<213> ORGANISM: Yellow fever virus 3'primer 2638

<400> SEQUENCE: 4
cgtggtggat ctggttgatt                                            20

<210> SEQ ID NO 5
<211> LENGTH: 20
<212> TYPE: DNA
<213> ORGANISM: Sindbis virus 5' primer SV1938

<400> SEQUENCE: 5
gagagcgcca cgttagtgta                                            20

<210> SEQ ID NO 6
<211> LENGTH: 20
<212> TYPE: DNA
<213> ORGANISM: Sindbis virus 3' primer SV2044

<400> SEQUENCE: 6
accttgtact gctcctcttc                                            20

<210> SEQ ID NO 7
<211> LENGTH: 18
<212> TYPE: DNA
<213> ORGANISM: respiratory syncytial virus M2-1 cloning primer 1

<400> SEQUENCE: 7
ccaaggatat ttgtcagg                                              18

<210> SEQ ID NO 8
<211> LENGTH: 26
<212> TYPE: DNA
<213> ORGANISM: respiratory syncytial virus M2-1 cloning primer 2

-continued

```
<400> SEQUENCE: 8
ggggcaaata tgtcacgaag gaatcc                                          26

<210> SEQ ID NO 9
<211> LENGTH: 20
<212> TYPE: DNA
<213> ORGANISM: luciferase 5' primer

<400> SEQUENCE: 9
catcacgtac gcggaatact                                                 20

<210> SEQ ID NO 10
<211> LENGTH: 20
<212> TYPE: DNA
<213> ORGANISM: luciferase 3' primer

<400> SEQUENCE: 10
cgcaactgca actccgataa                                                 20
```